Figure 1:
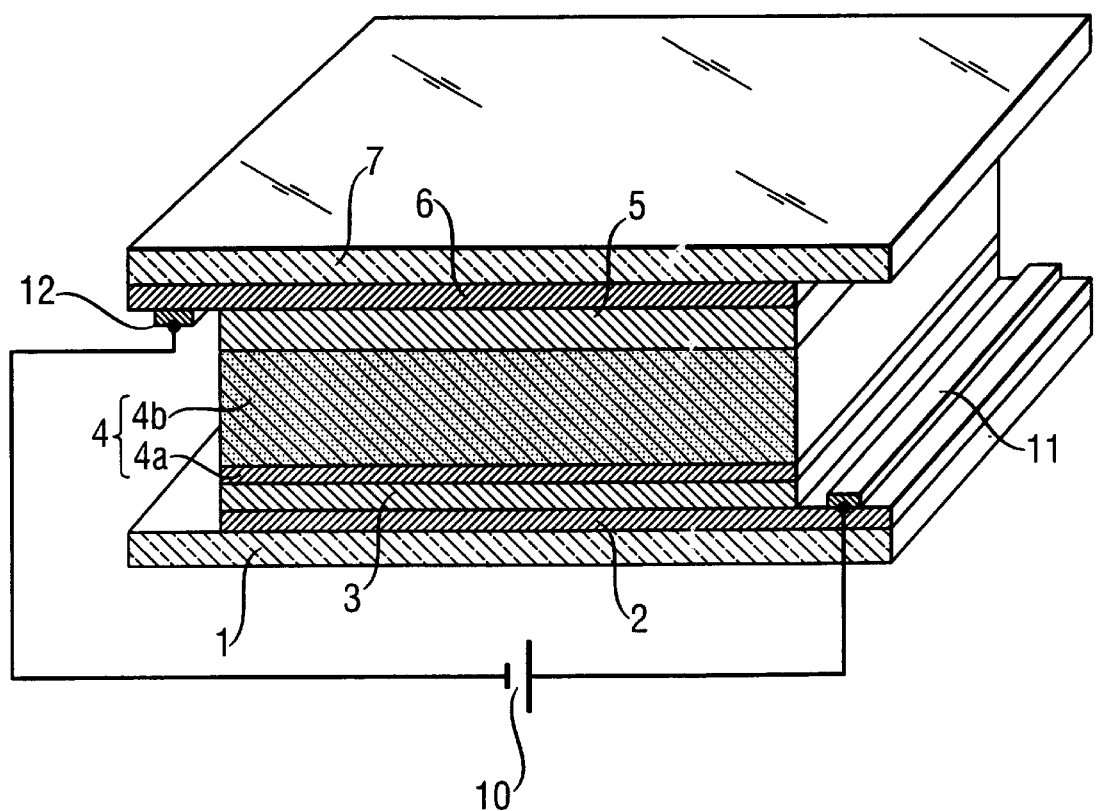

United States Patent [19]
Giron

[11] Patent Number: 5,985,486
[45] Date of Patent: Nov. 16, 1999

[54] ELECTROCHEMICAL DEVICE

[75] Inventor: Jean-Christophe Giron, Paris, France

[73] Assignee: Saint-Gobain Vitrage, Courbevoie, France

[21] Appl. No.: 08/933,141

[22] Filed: Sep. 18, 1997

[30] Foreign Application Priority Data

Sep. 18, 1996 [FR] France .................................. 96 11392

[51] Int. Cl.$^6$ .................................................. H01M 10/26
[52] U.S. Cl. .................... 429/188; 429/304; 429/231.95; 429/33
[58] Field of Search ..................................... 429/188, 219, 429/231.9, 231.95, 233, 304, 30, 33

[56] References Cited

U.S. PATENT DOCUMENTS

| | | | |
|---|---|---|---|
| 4,832,463 | 5/1989 | Goldner et al. .......................... | 350/357 |
| 4,888,258 | 12/1989 | Desjardins et al. ..................... | 429/194 |
| 5,186,813 | 2/1993 | Helms ..................................... | 205/171 |
| 5,731,105 | 3/1998 | Fleischer et al. ....................... | 429/192 |

*Primary Examiner*—Maria Nuzzolillo
*Assistant Examiner*—Angela J. Martin
*Attorney, Agent, or Firm*—Oblon, Spivak, McClelland, Maier & Neustadt, P.C.

[57] ABSTRACT

The subject of the invention is an electrochemical device which includes at least one substrate (1, 7), at least one electronically conductive layer (2, 6), at least one electrochemically active layer capable of inserting ions reversibly, especially cations of the $H^+$, $Li^+$, $Na^+$ and $Ag^+$ type, and an electrolyte. This electrolyte (4) comprises at least one layer of essentially inorganic material, of the oxide type, the ionic conduction of which is generated or increased by incorporating a hydrogen-containing and/or nitrogen-containing, in particular nitride-containing, compound or compounds.

33 Claims, 5 Drawing Sheets

ELECTROCHEMICAL DEVICE

The present invention relates to the field of electrochemical devices which include at least one electrochemically active layer capable of inserting ions and electrons reversibly and simultaneously, in particular electrochromic devices. These electrochemical devices are used, for example, to manufacture windows whose light and/or energy transmission or light reflection may be modulated by means of an electric current. They may also be used to manufacture energy storage elements, such as batteries, or gas sensors.

Taking the particular example of electrochromic systems, it will be recalled that these include, in a known manner, a layer of a material which is capable of inserting cations and electrons reversibly and simultaneously, the oxidation states of which material, corresponding to the inserted and ejected states, have a distinct colour, one of the states generally being transparent. The insertion or ejection reaction is controlled by a suitable electrical supply, for instance by applying an appropriate potential difference. The electrochromic material, generally based on tungsten oxide, must thus be brought into contact with an electron source, such as a transparent electronically conductive layer, and a cation source, such as an ionically conductive electrolyte.

Moreover, it is known that, in order to ensure at least about a hundred switching operations, there must be associated with the layer of electrochromic material a counterelectrode which is itself capable of reversibly inserting cations, symmetrically with respect to the layer of electrochromic material so that, macroscopically, the electrolyte appears as a single cation medium.

The counterelectrode must consist of a layer which is either neutral in colour or at least transparent when the electrochromic layer is in the decoloured state. Since tungsten oxide is a cathodic electrochromic material, that is to say that its coloured state corresponds to the most reduced state, an anodic electrochromic material, such as nickel oxide or iridium oxide, is generally used for the counterelectrode. It has also been proposed to use a material which is optically neutral in the two oxidation states in question, such as, for example, cerium oxide or organic materials such as electronically conductive polymers (polyaniline, etc.) or Prussian blue.

A description of such systems will be found, for example, in European Patents EP-0,338,876, EP-0,408,427, EP-0,575,207 and EP-0,628,849.

Currently, these systems may be arranged in two categories, depending on the type of electrolyte which they use:

either the electrolyte is in the form of a polymer or of a gel, for example a polymer exhibiting protonic conduction, such as those described in European Patents EP-0,253,713 and EP-0,670,346, or a polymer exhibiting lithium-ion conduction, such as those described in Patents EP-0,382,623, EP-0,518,754 or EP-0,532,408;

or the electrolyte is an inorganic layer, which is ionically conductive but electronically insulating; these systems are then referred to as "all-solid" electrochromic systems.

It has also been proposed, in Patent FR 96/03799 filed on Mar. 27, 1996 (corresponding to European Patent EP-97.400702.3 of Mar. 27, 1997), to use an electrolyte having one or more layers, including at least one electrochemically active layer capable of inserting the ions reversibly, in particular cations of the $H^+$, $Li^+$, $Na^+$ and $Ag^+$ type, but the overall oxidation state of which is essentially maintained constant, either by electrically isolating it from at least one of the electron sources of the device, for instance by combining it with a layer which is electronically insulating but is nevertheless ion-permeable, or by adjusting the electrical supply of the device, so that the potential of the layer is maintained at values outside the range of potentials which would cause a variation in the level of ion insertion of its constituent material.

All these electrochemical devices allow satisfactory reversibility of the ion insertion/ejection phenomena, and therefore of the colouring/decolouring phenomena, in the specific case of electrochromic systems. However, it seems that there could be a tendency for the reversibility characteristic to degrade over time, in particular because of prolonged exposure to ultraviolet radiation or to heat (for example when the temperature reaches 80° C.), or because of the large number (in particular greater than 100,000) of switching operations, going from a coloured state to another state.

This question has been studied in the aforementioned Patent EP-0,628,849, in which, more particularly in the case where the electrolyte is chosen in the form of a polymer, provision has been made to sandwich a "barrier layer" between the polymer electrolyte and the counterelectrode. This barrier layer, in particular an inorganic barrier layer of the tantalum oxide type, is a material which is sufficiently ionically conductive/ion-permeable in order not to hinder the transfer of cations from one electrochemically active layer to the other, but it does make it possible to limit the degradation of the system by slowing down the irreversible reduction of the counterelectrode, or even its dissolution in some cases, in contact with the polymer electrolyte.

Use is therefore made, as it were, just as in Patent PR 96/03799, of electrolytes which consist in fact not of a single layer, but optionally of a multilayer stack, if "electrolyte" is understood to mean the combination of ionically conductive layers lying between the electrode and counterelectrode or, expressed differently, between the two electrochemically active layers of the system. Moreover, there is at least one layer of the inorganic type in this stack, the most frequent embodiment being a layer in the form of an oxide. In this situation in particular, this layer of the electrolyte has an oxidation state which remains essentially constant during operation of the system.

It is therefore found that many electrochemical systems in particular of the electrochromic-system type, have henceforth had recourse, in order to form their electrolyte, to materials exhibiting an ionic conduction function which are of the inorganic type and which supplement or replace organic conductive materials of the polymer type.

The object of the invention is therefore to succeed in improving the ionic conductivity of this type of material so as to improve the performance characteristics of the electrolyte of the previously described electrochemical devices.

The subject of the invention relates to an electrochemical device which includes at least one substrate, at least one electronically conductive layer, at least one electrochemically active layer capable of inserting ions reversibly, in particular cations of the $H^+$, $Li^+$, $Na^+$ and $Ag^+$ type, and an electrolyte. The invention consists of the fact that the electrolyte comprises at least one layer of essentially inorganic material, of the oxide type, the ionic conduction of which is generated or increased by incorporating a hydrogen-containing and/or nitrogen-containing, in particular nitride-containing, compound or compounds.

The term "electrolyte" has been defined above as being the material or the combination of materials which will transfer the ions reversibly inserted by the electrochemically active layer or layers of the system.

The term "compound" denotes any element, functional group or molecule, of inorganic, organic or inorganic/organic "hybrid" origin, which is capable of introducing hydrogen and/or nitrogen atoms into the layer, either by incorporating the compounds "as they are" into the layer or by "releasing" the functional groups carrying nitrogen and/or hydrogen atoms coming from the said compounds in the layer.

This is because it has been found that it was possible to control, and more particularly to increase significantly, the ionic conduction of this type of material by "doping" it as it were with compounds having H and/or N atoms, even if the exact mechanism causing such an improvement is complex and has not yet been completely elucidated.

Advantageously, these compounds have at least one relatively labile hydrogen atom H, bonded covalently or ionically to a carbon, nitrogen, oxygen, phosphorous or sulphur atom.

They may, in particular, be a Brønsted-Lowry acid or a Brønsted-Lowry base.

As hydrogen-containing compound, mention may be made of organic compounds having a hydroxyl, carboxylic, ketone/enol, aldehyde and hydroperoxide functional groups. It is thus possible to mention ethanol, methanol, formaldehyde, formic acid and acetic acid.

They may also be nitrogen-containing compounds of the amine, imine, hydrazine, $N_2O$, or ammonia $NH_3$ type.

The two preferred compounds according to the invention are water $H_2O$ and ammonia $NH_3$ (hydrogen peroxide $H_2O_2$ could also be used).

As will be explained later, water is in fact a particularly useful and effective hydrogen-containing compound for improving the ionic conduction of a number of metal oxides, and several techniques for depositing layers can be used which allow precise control and selection of the water content in the layer according to various criteria.

Both water of adsorption and water of constitution may be used, and the metal oxide, once hydrated, may have in fact hydroxyl functional groups. In this more particular case, the presence of water in the layer is particularly recommended if the electrochemical device operates by reversible insertion of protons.

The invention does not apply just to layers of the oxide type but applies more generally to layers made of chalcogenides of transition, alkali, alkaline-earth and rare-earth metals. Preferably, layers are used based on at least one oxide of a metal belonging to the group of transition metals, especially those of Groups IVB and VB of the Periodic Table, and/or based on at least one oxide belonging to Groups IVA and VA of the Periodic Table. Particularly intended are, especially, chromium, indium, thorium, zirconium, hafnium, antimony, tantalum, titanium, germanium and silicon oxides and the mixed oxides of these metals, especially a tantalum/titanium mixed oxide, as well as the mixed oxides of these metals, combining with at least one oxide of one of these metals a metal oxide exhibiting the property of reversible cation insertion of the electrochromic type, such as the oxides of indium, niobium, bismuth, tungsten, nickel, cobalt, etc.

They may also be layers based on alumino-silicates, of the mica or feldspar type, or layers based on a heteropolyacid of the hydrated acid phosphate type such as $ZnO(H_3PO_4)_2 \cdot nH_2O$.

The invention may also apply to materials acting as an electrolyte, such as those described in Patent FR 96/03799 or the aforementioned EP-97.400702.3, i.e. ionically conductive materials capable of inserting the ions reversibly, but the overall oxidation state of which is maintained essentially constant. Reference should be made to the patent text for further details.

These materials may be arranged in two non-limiting categories, depending on the type of cations which they are able to insert, without distinguishing whether they are of the anodic or cathodic colouring type or whether they do not change colour depending on their level of insertion:

these materials may be suitable for inserting protons and may, in particular, include at least one of the following compounds: an oxide of tungsten W, of niobium Nb, of tin Sn, of bismuth Bi and of vanadium Va. They may also be nickel oxide or iridium oxide. These oxides may furthermore include an additional metal of the titanium, tantalum or rhenium type, the function of which can be varied. The additional metal may, for example, increase the hydrophilic nature of the oxide and, as a result, facilitate its hydration if the chosen hydrogen-containing compound according to the invention is water or includes hydroxyl functional groups.

these materials may be suitable for inserting lithium ions $Li^+$ and may, in particular, include at least one metal oxide which may or may not be lithiated, such as nickel oxide $NiO_x$, lithiated nickel oxide $LiNiO_x$, a mixture of titanium and cerium oxides $Ce/TiO_x$, and the oxides of tungsten, niobium, vanadium and iridium.

The layer according to the invention, once the hydrogen-containing and/or nitride-containing compounds have been incorporated, is therefore, in particular, in the form of a hydrated oxide or of an oxynitride which may or may not be hydrated, which layer may also include other elements, especially a halogen of the fluorine type. It has been noted, more particularly in the case of a layer based on tantalum, that it was advantageously possible to incorporate into it an agent suitable for enhancing its hydrophilic nature, in particular of the tungsten type.

The preferred embodiment of the layer according to the invention is a layer of hydrated tantalum oxide, of hydrated antimony oxide or of a hydrated mixed tantalum/tungsten oxide, or of a hydrated antimony/tungsten oxide.

The layer according to the invention may be chosen so that it is electronically insulating. This is an important property, in particular in the case where the layer may enable the other layer or layers making up the electrolyte to be electronically isolated from the electron sources of the device, for example in the configuration described in Patent FR 96/03799.

The electrochemical device incorporating the layer according to the invention in its electrolyte may be designed so that the electrolyte is in fact a multilayer stack. The stack may then include, in addition to the layer, at least one other layer of an essentially inorganic material. Moreover, it may include not one but at least two layers according to the invention, the simplest embodiment consisting in superposing, n times, two layers of hydrated oxide where n>0, of the (hydrated $Ta_2O_5$/hydrated $Sb_2O_5$)n type.

The electrolyte may thus be a multilayer electrolyte, and contain only layers of solid material. The "all-solid" electrolyte may also comprise at least two layers of solid material, especially sequences of two layers of the $WO_3/Ta_2O_5$ or $Sb_2O_5$, $NiO_x/WO_3$, $SnO_2/Ta_2O_5$, $SnO_2/Sb_2O_5$, $NiO_x/Ta_2O_5$, or $NiO_x/Sb_2O_5$ type, at least one of these oxides containing hydrogen and/or nitrogen in accordance with the invention, especially a hydrated oxide. Preferably, the monolayer or multilayer electrolyte of the invention has a maximum thickness of 5 μm, and especially of the order of 10 nm to 1 μm, especially for applications in electrochromic windows.

Within the context of the invention, by "solid material" is meant any material having the mechanical integrity of a solid, in particular any essentially inorganic or organic material or any hybrid material, i.e. a partly inorganic and partly organic material, such as the materials which may be obtained by sol-gel deposition from organo-inorganic precursors.

This therefore constitutes a so-called "all-solid" system configuration which has a clear advantage in terms of ease of manufacture. This is because, when the system contains an electrolyte in the form of a polymer which does not have the mechanical integrity of a solid, for example, it is necessary in fact to manufacture, in parallel, two "half-cells" each consisting of a carrier substrate coated with an electronically conducting first layer and then an electrochemically active second layer, these two half-cells then being joined together with the electrolyte being inserted between them. With an "all-solid" configuration, the manufacture is simplified since it is possible to deposit all the layers of the system, one after the other, on a single carrier substrate. Furthermore, this lightens the device since it is no longer essential to have two carrier substrates.

However, it may be preferred to have an electrolyte in the form of a multilayer stack which includes a different ionic conductor. This may be a layer of aqueous liquid, such as water to which there is added sulphuric or phosphoric acid, in the case of reversible insertion of protons, or a layer of an anhydrous liquid, such as propylene carbonate containing a lithium salt, in the case of reversible insertion of lithium ions.

There may also be a layer of gel or of polymer, especially protonically conductive polymers of the type consisting of a solid solution of polyoxyethylene and of phosphoric acid, POE-$H_3PO_4$ (in this case, the polymer also constitutes an electronic insulator), or else one based on a polymer obtained by the copolymerization of three precursors comprising two types of grafted trialkoxysilanes and a plasticizer having at least one urea functional group. As regards a polymer which conducts lithium ions, it is possible to choose an ionomer obtained by partial neutralization of polyacrylic acid, or a polymer based on a branched polyethyleneimine and on a lithium salt. For further details about the nature and synthesis of such polymer products, reference may advantageously be made to the patents mentioned in the preamble of the present application.

A multilayer electrolyte of the (layer according to the invention/POE-$H_3PO_4$) or (layer according to the invention/POE-$H_3PO_4$/layer according to the invention) type may thus be provided. This comes back to the teaching of the aforementioned Patent BP-0,628,849, the layers according to the invention avoiding acid contact of the polymer with the counterelectrode and thus preventing degradation of the latter. Hydrating these layers enables them to fulfil their barrier function effectively, without impairizing the performance of the electrolyte, since the invention enables their ionic conduction level to be adjusted with respect to that of the other materials of the electrolyte, in particular, in this case, with that of the polymer.

The invention relates not only to electrochemical devices employing the previously described electrolytes exhibiting improved ionic conductivity but also, independently of the latter, to these same devices employing improved electrochemically active layers; in order for these devices to operate, it is necessary to "inject" into the system the cations capable of being inserted reversibly. This may be achieved by immersing one of the electrochemically active layers, once it has been manufactured, in a bath containing the appropriate salts in solution. This so-called pre-insertion operation increases the time needed to manufacture the device, and there is always the fear of being unable to "dry" the layer sufficiently, once it has been removed from the bath. The invention proposes "in situ" pre-insertion of the said layer, i.e. during its actual manufacture, the best results having been achieved using layers of the $WO_3$ type, i.e. preferably exhibiting electrochromic properties of the cathodic-colouring type by reversible insertion of protons.

Its deposition process may be carried out using the same type of technique as for the previous electrolyte, in particular vacuum deposition of the sputtering type, the pre-insertion taking place by using a metal target and a reactive atmosphere using an oxidizing compound of the $O_2$ type and a compound capable of providing reversibly insertable protons of the $H_2$ type, etc. Preferably, hydrogen is introduced into an $O_2$/Ar atmosphere, finely controlling the conditions, especially the relative amounts of $H_2$ or $O_2$ introduced, in order finally to obtain the desired pre-insertion, this being different from the (non-reversible) hydration-type modification of the electrolyte mentioned previously. It is thus possible to manufacture a reduced oxide which is sufficiently pre-inserted: in the case of a layer based on tungsten oxide, current densities of the order of more than 0 to 0 to 20 $mC/cm^2$ per 100 nm thickness have been measured.

The invention also relates to all applications of the electrochemical device which has been described, there being in particular three of them:

the first application relates to electrochromic windows. In this case, advantageously, provision is made for the substrate or substrates of the device to be transparent, made of glass or plastic, when the windows are intended to operate in variable light transmission mode. If it is desired to give the window a mirror function, and for it to operate in variable light reflection mode, several solutions are possible: either one of the substrates is chosen to be opaque and reflective (for example a metal plate), or the device is combined with an opaque and reflective element, or one of the electronically conductive layers of the device is chosen so as to have a metallic nature and to be thick enough to be reflective.

In particular when the window is intended to operate in variable light transmission mode, using a device provided with one or two transparent substrates, it is possible to fit it as multiple glazing, especially as double glazing with another transparent substrate, and/or as laminated glass;

the second application relates to energy storage elements, most particular to batteries, which may be used, for example, in all appliances involving electronic and/or computing means, and all appliances requiring an energy storage device which is specific to them, autonomous or not;

the third application relates to gas sensors.

Epoxy-type seals are advantageously provided in order to seal the functional layers.

Returning to the first application, that of electrochromic windows, these may advantageously be employed both as windows for buildings, for motor vehicles, windows for industrial/public-transport vehicles, aircraft windows, railway windows, rear-view mirrors and other mirrors, or as optical elements such as camera lenses, or else as the front face, or an element to be placed on or near the front face of display screens of appliances such as computers and televisions.

In the electrochromic window application in particular, it has proved advantageous for the structure to be preferably a laminated structure of the type consisting of a rigid substrate (glass)/functional stack/polymer insert/rigid substrate (polycarbonate glass) or layers of the polyethylene terephthalate PET type.

The insert is preferably chosen to be one based on ethylene vinyl acetate (EVA) or on its copolymers, and it may also be made of polyurethane (PU), polyvinyl butyral (PBV), or a multicomponent or single-component resin which is thermally crosslinkable (epoxy or PU) or Uv-crosslinkable (epoxy or acrylic resin). The insert is important in the sense that it enables the functional stack to keep its degree of hydration constant, or at the very least sufficiently high in order to maintain its functionality, when it is exposed to high temperatures, which may be the case for the electrochromic windows used in exterior windows exposed to solar radiation. EVA has, in addition, the advantage of being able to be laminated at a lower temperature than, for example, PVB: on the one hand, there is no risk of embrittling the system during lamination and, on the other hand, it is protected from dehydration when exposed to the sun.

The devices of the invention which are used as batteries may also be employed in the field of buildings or vehicles, or form part of appliances of the computer, television or telephone type.

The invention also relates to the process for manufacturing the device according to the invention: the electrolyte layer of the invention forming part of the electrolyte may be deposited using a vacuum technique, of the sputtering type, optionally assisted by a magnetic field, using thermal evaporation, using plasma CVD (chemical Vapour Deposition) or using atmospheric-pressure techniques, in particular the deposition of layers using sol-gel synthesis, especially of the dipping, spray-coating or roll-coating type. It is also possible to use a liquid-phase or pulverulent-phase pyrolysis technique, or a gas-phase pyrolysis technique of the CVD type but at atmospheric pressure.

In fact, it is particularly advantageous in this case to use a vacuum deposition technique, especially of the sputtering type, since it allows very fine control of the amount of hydrogen-containing and/or nitrogen-containing compound or compounds which it is desired to obtain in the layer once it has been deposited.

It also enables this amount to be optimally adjusted depending on the type of material of which the layer is composed, in order to achieve the maximum ionic conductivity.

Thus, it is possible to deposit the electrolyte layer by reactive sputtering, in an atmosphere containing the nitrogen-containing and/or hydrogen-containing compounds or their "precursors". "Precursors" is understood to mean the molecules or compounds which are suitable for interacting and/or decomposing under certain conditions in order to form the desired hydrogen-containing and/or nitrogen-containing compound in the layer. Thus, if the hydrogen-containing compound is water and if it is desired to manufacture a layer of hydrated oxide, it is possible to choose to deposit the layer by sputtering in a reactive atmosphere containing either, directly, water vapour with or without a carrier gas, or water "precursors", such as a mixture of $H_2$ and $O_2$ in judicious proportions. The atmosphere may furthermore include any other gas, in particular one capable of increasing the sputtering rate of the target; this may be argon Ar, xenon Xe, neon Ne or other inert gases of the nitrogen $N_2$ type. When a sputtering atmosphere containing a $H_2/O_2$ mixture is chosen, some of the accelerated ions have, in fact, an energy sufficient to break the H—H bonds of hydrogen and the O—O bonds of oxygen, and thus allow the in situ formation of water vapour suitable for being incorporated in the layer being formed. The energy necessary to break these H—H and O—O bonds may be provided by the species excited by the plasma or generated by the target of the metal whose oxide it is desired to form, or by any other source, for example an ancillary plasma.

From an industrial standpoint, it is preferred to use a plasma in the presence of an $H_2/O_2$ mixture rather than to introduce water vapour directly. This is because its implementation is easier, and it has proved to be the case that there is better control of the homogeneity of the degree of hydration of the layer through its thickness over the entire surface area of the substrate to be coated. Moreover, there is less risk of "contaminating" the sputtering chamber with residual water. This also allows better control of the conductivity of the layer, as it is possible to adjust not only the content of the $H_2/O_2$ mixture in the sputtering atmosphere but also the relative proportions of $H_2$ and $O_2$ in the mixture. To do this, an $N_2O/H_2$ mixture can also be used.

In order to deposit a nitride-containing electrolyte layer according to the invention, a gas of the $NH_3$ type may be introduced into the sputtering chamber.

It is also possible to deposit the electrolyte layer according to the invention by thermal evaporation, as mentioned previously. It may be assisted by an electron beam, the hydrogen-containing and/or nitrogen-containing compounds or their "precursors" being introduced into the layer in gas form and/or being contained in the material intended to be evaporated.

The electrolyte layer according to the invention may also be deposited using a technique of the sol-gel type. The content of hydrogen-containing and/or nitrogen-containing compounds is controlled by various means: it is possible to adapt the composition of the solution, so that it contains these compounds or their "precursors", and that of the atmosphere in which the deposition takes place. This control may also be refined by adjusting the temperature of deposition/curing of the layer.

Figure 2:
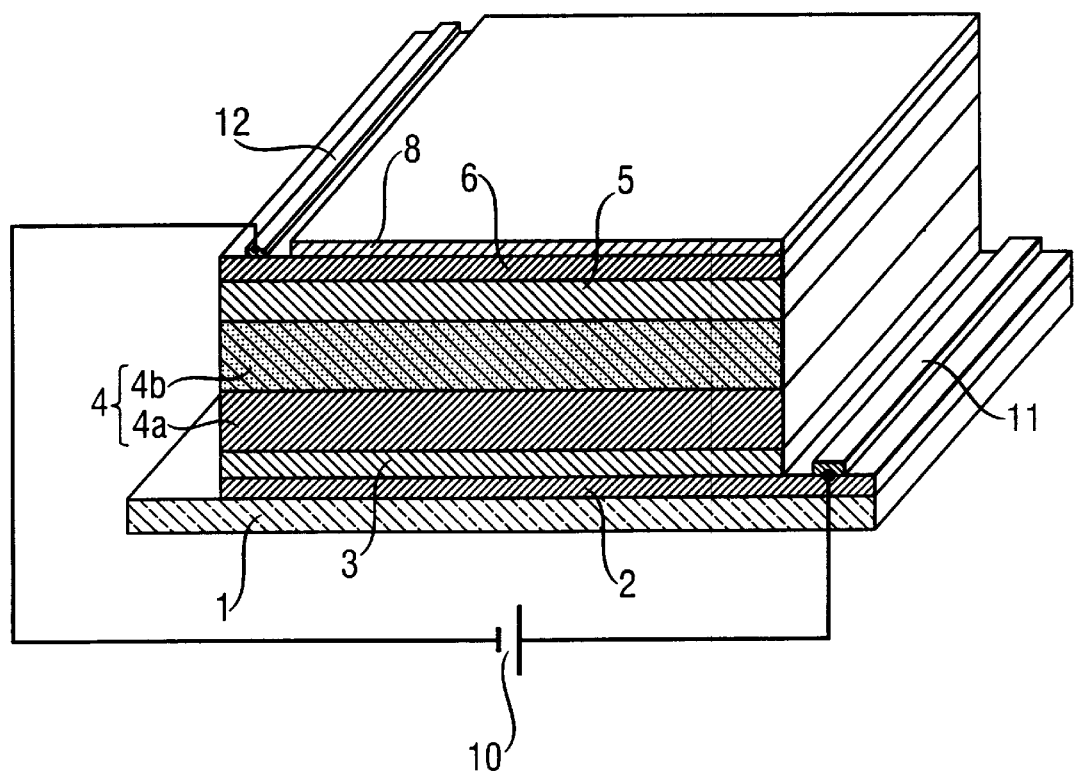
Figure 3:
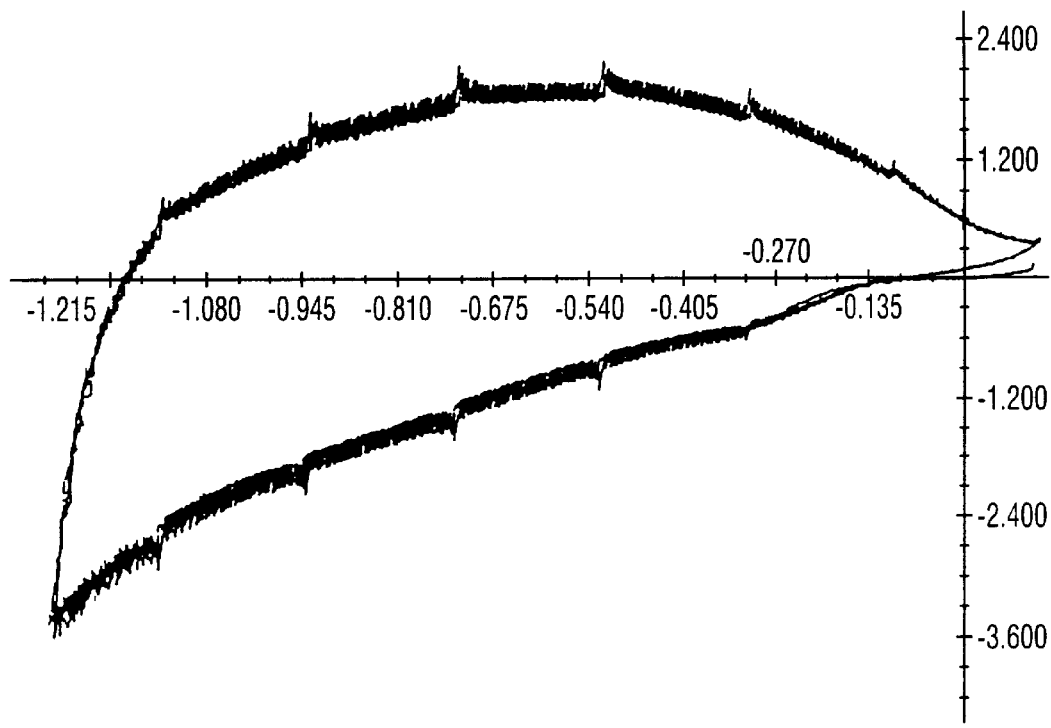
Figure 4:
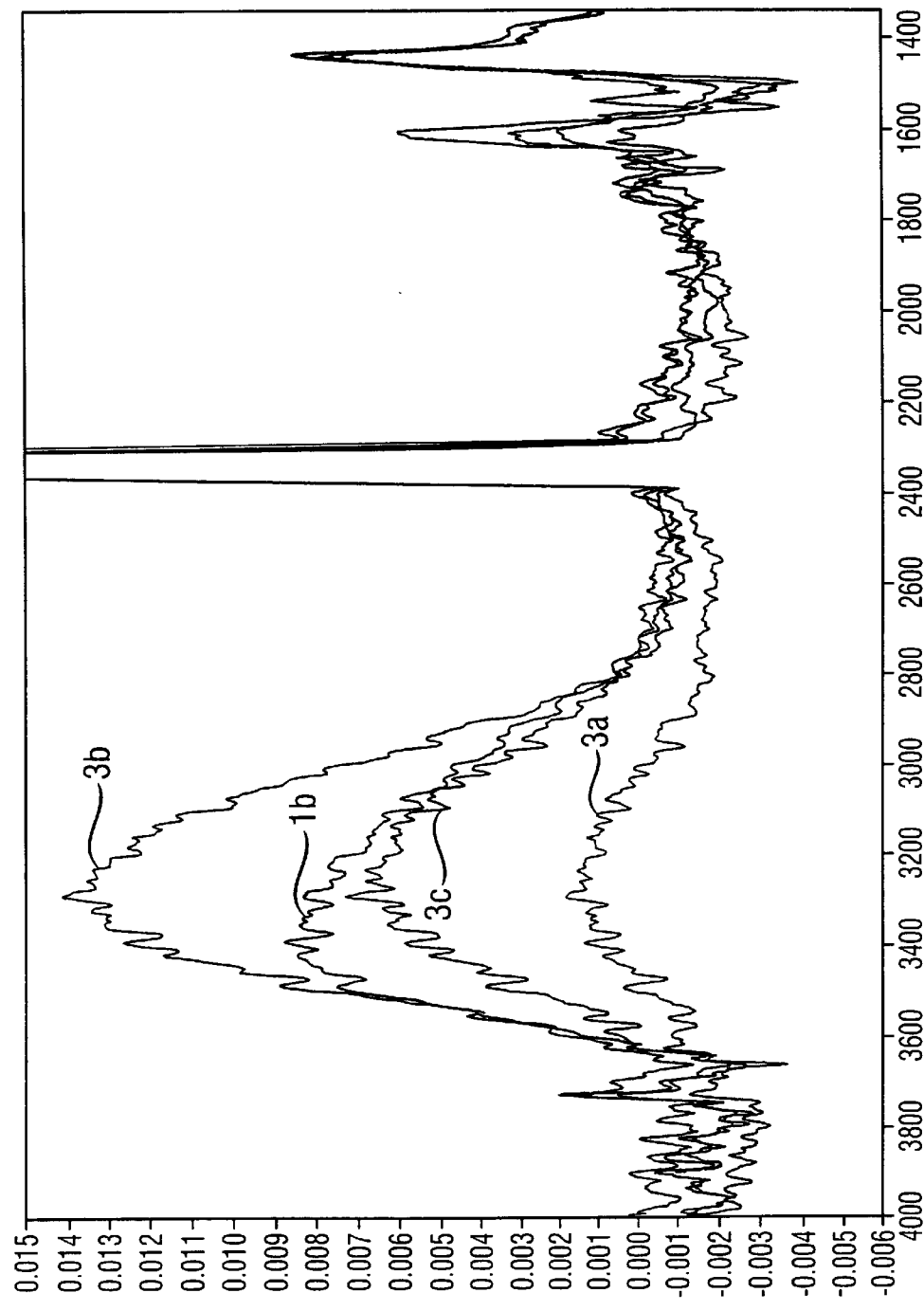
Figure 5:
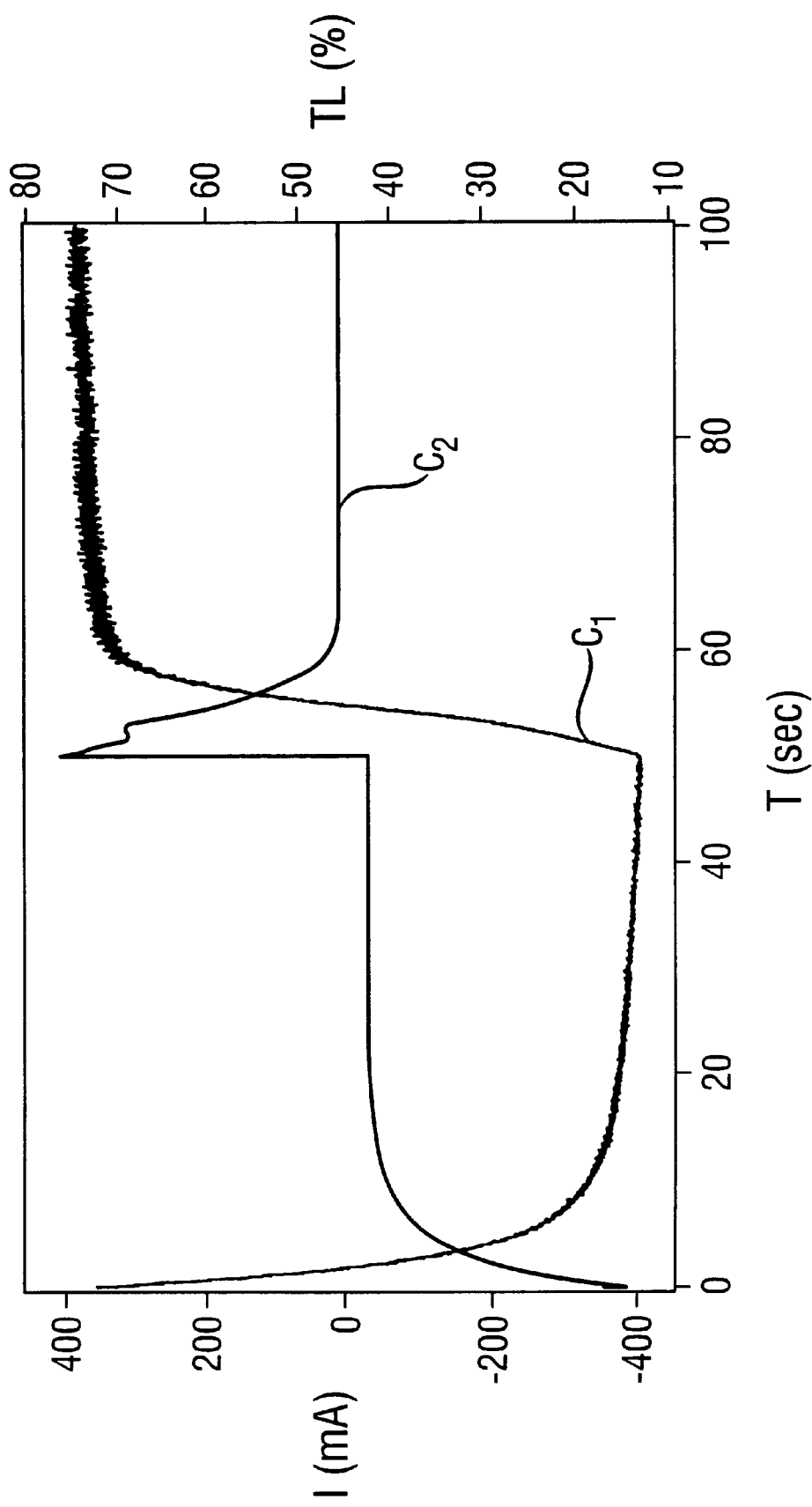

Further details and advantageous characteristics of the invention will emerge from the description given below with reference to the appended drawings which represent:

FIG. 1: a representation of a first embodiment of an electrochromic window according to the invention;

FIG. 2: a representation of a second embodiment of an electrochromic window according to the invention;

FIG. 3: a voltammogram of a window as in FIG. 1;

FIG. 4: an FTIR (Fourier transform infrared) analysis curve for the layers according to the invention; and FIG. 5: a graph showing the operation of an electrochromic window according to the invention.

FIGS. 1 and 2 are extremely diagrammatic and do not respect the proportions between the various elements shown, this being done for the sake of clarity.

Before beginning a detailed description thereof, three types of layers according to the invention, which are suitable for acting as an electrolyte in an electrochromic window, are described. These three types of layers have been deposited identically on various substrates so as to be able to carry out certain analyses: they have been deposited on a silicon substrate, polished on both its sides in order to carry out FTIR analysis on them, on a substrate made of silica-soda-lime glass covered with a thin layer of nickel-chromium in order to determine their ionic conductivity by impedance measurement. Finally, for the purpose of incorporating them into an electrochromic window as the electrolyte, they have been deposited on a substrate of silica-soda-lime glass 4 mm in thickness which is covered with an electronically conductive layer, optionally with a layer exhibiting electrochromic properties and/or with a layer which also forms part of the electrolyte, the layer on which the layer according to the invention is deposited being determined by the configuration of the electrochromic system envisaged.

All the layers according to the invention in Examples 1 to 3 which follow are based on metal oxide(s) and deposited by reactive sputtering using a metal target in the presence of oxygen.

EXAMPLE 1

A first type of layer is a layer of hydrated tantalum oxide, denoted for convenience by $Ta_2O_5.nH_2O$. (Within the framework of this application, the incorporation of water in an oxide will be denoted $nH_2O$, whether or not this reflects the reality, since it is not possible to distinguish in this notation whether it is water of adsorption, water of crystallization and/or whether in fact it is a hydroxide with hydroxyl functional groups).

This layer is deposited by magnetic-field-assisted sputtering, the reactive sputtering using a target of metallic tantalum.

Example 1a: the deposition was carried out a first time, by way of comparison, in a reactive atmosphere exclusively composed of an $Ar/O_2$ mixture for the purpose of obtaining a non-hydrated oxide.

Example 1b: this deposition was carried out in an $Ar/O_2/H_2$ atmosphere.

Example 1c: the deposition was carried out in an $Ar/O_2/H_2O$ atmosphere.

EXAMPLE 2

The second type of layer is a layer based on hydrated antimony oxide, $Sb_2O_5.nH_2O$. It is deposited by the same technique as for Example 1, using a target of metallic Sb.

Example 2a: the deposition was carried out a first time, by way of comparison, in a reactive atmosphere exclusively composed of an $Ar/O_2$ mixture.

Example 2b: this deposition was carried out in an $Ar/O_2/H_2$ atmosphere.

Example 2c: the deposition was carried out in an $Ar/O_2/H_2O$ atmosphere.

EXAMPLE 3

The third type of layer is a layer based on tantalum oxide which is hydrated and to which tungsten is incorporated, this layer, by convention, being denoted by $TaWO_x.nH_2O$ and deposited by the same deposition technique as for the two previous examples, using a target of a Ta—W alloy having a relative mass proportion of tungsten of 5%.

Example 3a: the deposition was carried out a first time, by way of comparison, in a reactive atmosphere exclusively composed of an $Ar/O_2$ mixture.

Example 3b: this deposition was carried out in an $Ar/O_2/H_2$ atmosphere.

Example 3c: the deposition was carried out in an $Ar/O_2/H_2O$ atmosphere.

The deposition conditions for these 6 layers are summarized in Table 1 below which, for each of them, indicates the nature of the material deposited, the flow rate of the gases introduced into the sputtering chamber in $cm^3/min$ under standard conditions, the total pressure within the sputtering chamber expressed in pascals and the power used in watts. The layers are deposited with thicknesses preferably lying between 20 and 300 nm, these being adjusted in order to allow correct measurement using FTIR and impedometry. (When they are incorporated in an electrochromic window, their thicknesses will be specified with the aid of Examples A and B which follow).

TABLE 1

| | Nature of the layer | Gas flow rate | Pressure | Power |
|---|---|---|---|---|
| Example 1a | $Ta_2O_5$ | Ar: 10<br>$O_2$: 7.7 | $4 \times 10^{-1}$ | 260 |
| Example 1b | $Ta_2O_5.nH_2O$ | Ar: 20<br>$O_2$: 2<br>$H_2$: 10 | 1 | 186 |
| Example 1c | $Ta_2O_5.nH_2O$ | Ar: 20<br>$O_3$: 2<br>$H_2O$: 2.2 | 2 | 156 |
| Example 2a | $Sb_2O_5$ | Ar: 20<br>$O_3$: 7 | 2 | 90 |
| Example 2b | $Sb_2O_5.nH_2O$ | Ar: 20<br>$O_2$: 8<br>$H_2$: 10 | 2 | 87 |
| Example 2c | $Sb_2O_5.nH_2O$ | Ar: 20<br>$O_2$: 6<br>$H_2O$: 2.2 | 2 | 89 |
| Example 3a | $TaWO_x$ | Ar: 20<br>$O_2$: 4 | 1 | 157 |
| Example 3b | $TaWO_x.nH_2O$ | Ar: 20<br>$O_2$: 10<br>$H_2$: 10 | 1 | 130 |
| Example 3c | $TaWO_x.nH_2O$ | Ar: 20<br>$O_2$: 10<br>$H_2O$: 2.2 | 1 | 140 |

Table 2 below recapitulates, for each of these six layers:

their water content, measured by FTIR analysis by the area of the peaks corresponding to the absorptions due to the symmetric vibration of the OH bonds. This content, expressed without any units, is merely an evaluation, but it does allow comparisons to be made from one layer to another;

their proton conductivity, determined by complex impedance measurement, expressed in the units $ohm^{-1}.cm^{-1}$.

TABLE 2

| | Nature of the layer | Water content | Proton conductivity |
|---|---|---|---|
| Example 1a | $Ta_2O_5$ $(Ar/O_2)$ | 0 | $9 \times 10^{-9}$ |
| Example 1b | Hydrated $Ta_2O_5$ $(Ar/O_2/H_2)$ | 2.79 | $3.4 \times 10^{-5}$ |
| Example 1c | Hydrated $Ta_2O_5$ $(Ar/O_2/H_2O)$ | 2.24 | $2.5 \times 10^{-5}$ |
| Example 2a | $Sb_2O_5$ $(Ar/O_2)$ | 1.98 | $1.2 \times 10^{-5}$ |
| Example 2b | Hydrated $Sb_2O_5$ $(Ar/O_2/H_2)$ | 8.14 | $7.3 \times 10^{-5}$ |
| Example 2c | Hydrated $Sb_2O_5$ $(Ar/O_2/H_2O)$ | 7.14 | $2.0 \times 10^{-5}$ |
| Example 3a | $TaWO_x$ $(Ar/O_2)$ | 1.62 | $1.8 \times 10^{-5}$ |
| Example 3b | Hydrated $TaWO_x$ $(Ar/O_2/H_2)$ | 3.47 | $5.9 \times 10^{-5}$ |
| Example 3c | Hydrated $TaWO_x$ $(Ar/O_2/H_2O)$ | 3.03 | $3 \times 10^{-5}$ |

From this Table 2 and more particularly from the results for Example 1, it may be seen that in the absence of hydration, a layer of the tantalum oxide type is in fact extremely ionically insulating: without the controlled hydration carried out according to the invention, this layer is a priori unusable as an electrolyte, unless it is structurally modified, for example by promoting columnar crystalline growth which creates sufficient porosity for the layer to be ion-permeable. However, this is very difficult to control, and even more difficult to optimize. In contrast, the invention allows precise adjustment of the ionic conductivity of the layer to values which are quite sufficient for the function which it is desired for them to fulfil, by controlling its degree of hydration.

Examples 2 and 3 illustrate the case in which the invention enables an already existing, but insufficient, proton conductivity to be improved. In both cases, it is with a reactive atmosphere using an $O_2/H_2$ mixture, in order to generate water in situ, that the highest proton conductivities are obtained.

FIG. 4 shows the PTIR analysis curves for the layers according to Examples 3a, 3b, 3c and 1b. Indicated as the abscissae are the wavenumbers in $cm^{-1}$ and as ordinates the absorbances. The degree of hydration is indicated by the height of the peaks which occur between approximately 3650 and 2800 $cm^{-1}$, these peaks corresponding to vibrations of the O—H bonds. It may be verified that a high proton conductivity correlates with a significant water content.

These three types of layers, which are not limiting, may therefore advantageously be incorporated into monolayer or multilayer electrolytes of electrochromic windows, such au those shown in FIGS. 1 and 2.

FIG. 1 corresponds to an electrochromic window whose electrolyte contains a polymer (Example A). FIG. 2 corresponds to an "all-solid" electrochromic window (Example B).

EXAMPLE A

Example A corresponds to the window shown in FIG. 1, which is a window operating by proton transfer. It consists of a first glass substrate 1, made of silica-soda-lime glass 4 mm in thickness, followed in succession by:

a first, electronically conductive layer 2 of $F:SnO_2$, 300 nm in thickness;

a first layer 3 of anodic electrochromic material, made of hydrated nickel oxide $NiO_xH_y$, 185 nm in thickness, (it could be replaced by a layer of hydrated iridium oxide 55 nm in thickness);

an electrolyte 4 which is divided into a first layer 4a of hydrated tantalum oxide according to Example 1b, 70 nm in thickness, a second layer 4b of a solid solution of polyoxyethylene with phosphoric acid $POE-H_3PO_4$, 100 micrometres in thickness, or alternatively a solid solution of polyethyleneimine with phosphoric acid, $PEI-H_3PO_4$;

a second layer 5 of cathodic electrochromic material based on tungsten oxide, 350 nm in thickness;

a second layer 6 of $F:SnO_2$, 300 nm in thickness, and then a second glass substrate 7 identical to the first.

Also shown are the current leads 11, 12 in the form of strips placed at the opposite ends of the two electronically conductive layers 2, 6 and electrically connected to a voltage generator 10.

This example, in accordance with the invention, therefore consists of a two-layer electrolyte based on a polymer normally used in this type of window, which is "coated" with a layer of hydrated tantalum oxide sufficiently conductive not to impede the transfer of protons via the polymer and which protects the counterelectrode of anodic electrochromic material from direct contact with the polymer, the intrinsic acidity of which would be prejudicial to it.

Instead of the hydrated $Ta_2O_5$ layer, the layer of the hydrated $Sb_2O_5$ or $TaWO_x$ type of Examples 2 and 3 may be used.

It is also possible to provide a three-layer electrolyte, having two layers of hydrated oxide according to the invention, either on each side of the polymer layer or superposed one on the other on the counterelectrode side.

EXAMPLE B

This example corresponds to the window shown in FIG. 2. It consists of a glass substrate 1 on which are deposited, one after the other, the following layers:

an electronically conductive layer 2 of ITO or $F:SnO_2$, 300 nm in thickness;

a layer 3 of cathodic electrochromic material, made of tungsten oxide $WO_3$, 350 nm in thickness;

a two-layer electrolyte 4 composed of a layer 4a of hydrated tantalum oxide and of a layer 4b of hydrated antimony oxide, each 100 nm in thickness;

a layer 5 of anodic electrochromic material made of nickel oxide $NiO_x$, approximately 200 nm in thickness, or of iridium oxide $IrO_x$ approximately 50 nm in thickness, these oxides being optionally hydrated;

an electronically conductive layer 6 of silver, 10 nm in thickness; and a combination of layers 8 whose purpose is to protect the subjacent silver layer, in particular from oxidation. This is preferably a thin layer of NiCr from 1 to 3 nm in thickness on top of which is a layer of material, for example a dielectric material, in particular one based on an oxide such as tin oxide, having a thickness of between 20 and 50 nm. (The NiCr layer makes it possible to protect the silver layer from oxidation during deposition of the $SnO_2$ layer by sputtering in the presence of oxygen. In the final window, it is therefore partly or completely oxidized). A second NiCr layer may also be optionally sandwiched between the silver layer 6 and the electrochemically active layer 5. (If the thickness of the silver layer is increased sufficiently, for example up to 30 to 50 nm, it is then possible to obtain an electrochromic window which no longer operates in transmission mode but in reflection mode, and therefore operates as a mirror: in this case, the observer looks at the window through the substrate 1 and sees its colour modification since the first electronically conductive layer 2 is transparent, the mirror reflective effect being obtained by the metallic second electronically conductive layer 6).

In this example, the window has a high performance "all-solid" two-layer electrolyte. It is entirely possible to use merely a single hydrated oxide layer instead of two. However, such a "two-layer" electrolyte may have certain advantages. Thus, it is possible to optimize as far as possible the nature of each of the oxides so that they provide maximum compatibility with each of the layers lying on either side of the electrolyte. Furthermore, it is possible to vary the manner by which each of the two layers of the electrolyte is formed, it being possible for the second layer to be nucleated in an appropriate manner on the first layer in order to provide the most appropriate structure for increasing the ion-permeability of the electrolyte in its entirety.

Furthermore, in the case of an "all-solid" electrolyte, it is preferable for the latter to be electronically insulating: in a multilayer structure, it may be sufficient for only one of the layers of the multilayer to satisfy this criterion.

The voltammogram in FIG. 3 makes it possible to "visualize" the current exchanged as a function of the voltage applied to the window according to Example A (with $PEI-H_3PO_4$ in the electrolyte). It shows a correct functionality of the system (the potential in volts is shown as the abscissae and the current in mA as the ordinates). The quantity of charge exchanged per cycle is 10 $mC/cm^2$ for an area of 28 $cm^2$. It should be noted that the window according to Example A, corresponding to the voltammogram, has, before possibly fitting it in double glazing, a light transmission value $T_L$ of 73% in the decoloured state and 8% in the coloured state, and colour values in transmission, according to the (L, a*, b*) colorimetry system, such that:

a*=−5.5 and b*=6.1 in the decoloured state a*=−5 and b*=−6.1 in the coloured state.

(The measurements are carried out under the $D_{65}$ illuminant).

EXAMPLE C

This Example C has a configuration similar to Example B, with a two-layer electrolyte, and is fitted into a laminated glass: a glass substrate 1 mm in thickness is provided in succession with:

a layer of ITO, 300 nm in thickness;

a layer of electrochromic material exhibiting anodic coloration, $IrO_x$, approximately 40 nm in thickness;

a two-layer electrolyte comprising a layer of $WO_3$, 200 nm in thickness, and a layer of hydrated tantalum oxide, 150 nm in thickness;

a layer of electrochromic material exhibiting cathodic coloration, based on $WO_3$, approximately 350 nm in thickness, deposited by sputtering in an $H_2/O_2$ plasma in order to carry out, in situ, its proton pre-insertion; it is thus directly in the reduced form, which can be checked by measuring a current density of approximately 20 $mC/cm^2$; and a final electronically conductive layer of ITO, 300 nm in thickness (the surface resistance of which, as in the previous case, being approximately 15 ohms per square).

The substrate thus coated is then laminated to a second glass, 1 mm in thickness, with an EVA-based sandwich sheet 1 mm in thickness.

Supplied by a voltage generator in a known manner with a voltage of −1.6 V, the light transmission $T_L$ of the window, in the coloured stated, is 6%, with a* and b* values in reflection in the (L, a*, b*) calorimetric system of respectively −0.6 and −25.6. In the decoloured state (+1.0 V), the $T_L$ is 76.5%, and the values of a* and b* in reflection are respectively −2.3 and +8.7.

FIG. 5 shows an operating cycle for the window: shown as abscissae is the time in seconds and as ordinates on the left-hand side is the current measured in mA and as ordinates on the right-hand side is the value of $T_L$. The curve $C_1$ represents the variations in $T_L$ and the curve $C_2$ the variations in current. The cycle is divided into a colouring first phase followed by a decolouring second phase.

A very high contrast is therefore obtained with such an electrochromic window; it the contrast is defined by the ratio of $T_L$ in the decoloured state to $T_L$ in the coloured state, it is more than 10, more precisely 12.75, this being an excellent result, and the durability, especially the thermal durability, of the system is furthermore guaranteed by the lamination with the sheet of EVA.

Many other electrochromic devices may use monolayer or multilayer electrolytes according to the invention. Without, of course, being exhaustive, mention may be made, for example, of electrochromic windows of the following type of configuration:

a: glass-type substrate
b: electronically conductive layer
c: cathodic colouring material of the $WO_3$ type
d: multilayer electrolyte:
   $d_1$: $Ta_2O_5.nH_2O$ or $Sb_2O_5.nH_2O$ (layer according to the invention),
   $d_2$: cathodic colouring material of the $WO_3$ type, optionally hydrated, but maintained at a constant oxidation state by the presence of $d_1$ which is sandwiched between c and $d_2$
e: anodic colouring material of the $NiO_x$ or $IrO_x$ type
f: electronically conductive layer
g: optionally, a second substrate Symmetrically, it is possible to have the following type of configuration:
a: glass-type substrate
b: electronically conductive layer
c: cathodic colouring material of the $WO_3$ type
d: multilayer electrolyte:
   $d_1$: anodic colouring material, of the $NiO_xH_y$ type but maintained at a constant oxidation state by the presence of $d_2$
   $d_2$: layer according to the invention, of the $Ta_2O_5.nH_2O$ type
e: anodic colouring material of the $NiO_xH_y$ type
f: electronically conductive layer
g: optionally, a second substrate It is also possible to have a configuration such that a single layer (e, f) of metal, more particularly based on gold Au, replaces the anodic colouring material e and the electronically conductive layer f.

I claim:

1. Electrochemical device which includes at least one substrate, at least one electronically conductive layer, at least one electrochemically active layer capable of inserting ions reversibly, in particular cations of $H^+$, $Li^+$, $Na^+$ $Ag^+$, and an electrolyte, characterized in that the electrolyte comprises at least one layer of essentially inorganic of the oxide type material of the oxide type, the ionic conduction of which is generated or increased by incorporating at least one of a hydrogen-containing and nitrogen-containing, and nitride-containing, compound or compounds.

2. Device according to claim 1, characterized in that the hydrogen-containing compound or compounds have at least one labile hydrogen atom H, bonded covalently or ionically to a carbon atom C, a nitrogen atom N, an oxygen atom O, a phosphorous atom P or a sulphur atom S.

3. Device according to claim 1, characterized in that the hydrogen-containing and/or nitrogen-containing compound (s) comprises/comprise at least one Brønsted-Lowry acid or a Brønsted-Lowry base.

4. Device according to claim 1, characterized in that the hydrogen-containing compound(s) comprises/comprise an organic compound having a hydroxyl, carboxylic, ketone/enol, aldehyde or hydroperoxide functional group.

5. Device according to claim 1, characterized in that the hydrogen-containing and/or nitrogen-containing compound or compounds comprises/comprise nitrogen, in particular in the form of amine, imine, hydrazine, $N_2O$ or ammonia $NH_3$.

6. Device according to claim 1, characterized in that the hydrogen-containing compound or compounds comprises/comprise water $H_2O$ or hydrogen peroxide $H_2O_2$.

7. Device according to claim 6, characterized in that the hydrogen-containing compound is water $H_2O$, in particular incorporated in the form of water of adsorption and/or water of constitution of the oxide or of the mixture of oxides of which the layer of the electrolyte is composed.

8. Device according to claim 1, characterized in that the layer having a hydrogen-containing and/or nitrogen-containing compound or compounds is based on a chalcogenide of transition, alkali, alkaline-earth or rare-earth metals.

9. Device according to claim 1, characterized in that the layer having a hydrogen-containing and/or nitrogen-containing compound or compounds is based on at least one oxide belonging to the family of oxides of transition metals, especially those of Groups IVB and VB of the Periodic Table and/or Groups IVA and VA of the Periodic Table, especially of the type comprising chromium oxide, indium oxide, thorium oxide, zirconium oxide, hafnium oxide, antimony oxide, tantalum oxide, titanium oxide, germanium oxide, silicon oxide and mixed oxides of these metals, such as a tantalum/titanium mixed oxide, or a mixed oxide of one of these metals with a metal oxide exhibiting properties of reversible ion insertion of the electrochromic type.

10. Device according to claim 1, characterized in that the layer having a hydrogen-containing and/or nitrogen-containing compound or compounds is based on alumino-silicates of the mica or feldspar type.

11. Device according to claim 1, characterized in that the layer having a hydrogen-containing and/or nitrogen-containing compound or compounds is based on a heteropolyacid of the acid phosphate type, especially of the $Zno(H_3PO_4)_2 \cdot nH_2O$ type.

12. Device according to claim 1, characterized in that the layer having a hydrogen-containing and/or nitrogen-containing compound or compounds is based on an ionically conductive material capable of inserting protons reversibly but whose overall oxidation state is maintained essentially constant, which includes in particular at least one of the following compounds: the oxides of tungsten W, of niobium Nb, of tin Sn, of bismuth Bi, of vanadium Va, of nickel Ni and of iridium Ir, and comprising, optionally, an additional metal such as titanium, tantalum or rhenium.

13. Device according to claim 1, characterized in that the layer having a hydrogen-containing and/or nitrogen-containing compound or compounds is based on a material capable of inserting lithium ions $Li^+$ reversibly but whose oxidation state is maintained essentially constant, in particular one based on at least one metal oxide which may or may not be lithiated, such as nickel oxide $NiO_x$, lithiated nickel oxide $LiNiO_x$, a mixture of titanium and cerium oxides $Ce/TiO_x$, and the oxides of tungsten W, niobium Nb, vanadium Va and iridium Ir.

14. Device according to claim 1, characterized in that the layer having a hydrogen-containing and/or nitrogen-containing compound or compounds is in the form of a hydrated oxide or of an oxynitride which may or may not be hydrated, optionally also containing a halogen of the fluorine type, especially of the hydrated tantalum oxide, hydrated antimony oxide or hydrated mixed tantalum/tungsten oxide or hydrated mixed antimony/tungsten oxide type.

15. Device according to claim 1, characterized in that the layer having a hydrogen-containing and/or nitrogen-containing compound or compounds is electronically insulating.

16. Device according to claim 1, characterized in that the electrolyte is a multilayer stack which includes, in addition to the layer having a hydrogen-containing and/or nitrogen-containing compound or compounds, at least one other layer of an essentially inorganic material.

17. Device according to claim 1, characterized in that the electrolyte is a multilayer stack comprising at least two layers having a hydrogen-containing and/or nitrogen-containing compound or compounds, especially in the form of a (hydrated $Ta_2O_5$/hydrated $Sb_2O_5$)n sequence where n>0.

18. Electrochemical device according to claim 1, characterized in that the electrolyte is a multilayer electrolyte, the latter and preferably all of the layers of the said device containing only layers of solid material, especially an electrolyte of the $WO_3/(Ta_2O_5$ or $Sb_2O_5)$ or (nickel oxide/$WO_3$) or ($SnO_2/Ta_2O_5$), ($SnO_2/Sb_2O_5$), ($NiO_x/Ta_2O_5$) or ($Nio_x/Sb_2O_5$) type, at least one of these oxides containing hydrogen and/or nitrogen.

19. Device according claim 1, characterized in that the electrolyte is a multilayer stack which also includes a layer of an ionically conductive material chosen in the form of an anhydrous or aqueous liquid or a liquid based on a gel or gels, or on a polymer or polymers, especially an electrolyte of the (layer having a hydrogen-containing and/or nitrogen-containing compound or compounds/POE:$H_3PO_4$) type.

20. Device according to claim 1, characterized in that at least one of the electrochemically active layers, especially that exhibiting cathodic colouring electrochromic properties, of the $WO_3$ type, is pre-inserted with cations, especially with protons, while it is being formed.

21. Electrochromic window, characterized in that it includes the electrochemical device according to claim 1, having in particular a variable light and/or energy transmission, with the transparent substrate or all the transparent substrates made of glass or plastic, preferably fitted into multiple glazing and/or laminated glass.

22. Energy storage element, characterized in that it includes the electrochemical device according to claim 1.

23. Gas sensor, characterized in that it includes the electrochemical device according to claim 1.

24. Process for manufacturing an electrochemical device according to claim 1, characterized in that the layer having a hydrogen-containing and/or nitrogen-containing compound or compounds of the electrolyte is deposited using a vacuum technique of the sputtering, evaporation or plasma CVD type or using synthesis via a sol-gel route, especially of the dipping, spray-coating or roll-coating type, or else liquid-phase or pulverulent-phase or gas-phase pyrolysis.

25. Process according to claim 24, characterized in that the layer having a hydrogen-containing and/or nitrogen-containing compound or compounds is deposited using reactive sputtering in an atmosphere containing the hydrogen-containing and/or nitrogen-containing compounds, or the "precursors" of the said compounds, especially, in the case of an electrolyte in the form of a hydrated oxide, in an atmosphere containing $H_2O$ or an $H_2/O_2$ mixture or else an $N_2O/H_2$ mixture; and, in the case of an electrolyte in the form of a nitride-containing oxide, in an atmosphere containing $NH_3$.

26. Process according to claim 24, characterized in that the layer having a hydrogen-containing and/or nitrogen-containing compound or compounds is deposited using thermal evaporation, optionally assisted by an electron beam, the hydrogen-containing and/or nitrogen-containing compounds or their "precursors" being introduced into the layer in gaseous form and/or being contained in the material intended to be evaporated.

27. Process according to claim 24, characterized in that the layer having a hydrogen-containing and/or nitrogen-containing compound or compounds is deposited by synthesis via a sol-gel route, by controlling the content of hydrogen-containing and/or nitrogen-containing compound or compounds of the layer by the choice of the composition of the solution, the atmosphere during deposition and/or the temperature of deposition/temperature of curing of the layer.

28. Process according to claim 24, characterized in that at least one of the electrochemically active layers is deposited using a vacuum technique, especially using reactive sputtering under conditions allowing its pre-insertion, during its deposition, with cations.

29. Use of the electrochromic window according to claim 21 as a window for a building, a window for a motor vehicle, a window for industrial or public-transport vehicles, a railway window, an aircraft window, rear-view mirrors and other mirrors, as optical components such as camera lenses, as the front face or element to be arranged on the front face of display screens of appliances such as computers or televisions.

30. Use of the energy storage element according to claim 22 in appliances involving electronic and/or computing means and in appliances requiring an energy storage device which is specific to them, autonomous or not, especially computers, televisions or telephones.

31. The electrochemical device according to claim 1 further comprising at least one seal made of epoxy resin.

32. The electrochromic window according to claim 21 having a laminated structure of one of a first and second type structure wherein said first type structure comprises, in order, a first rigid substrate, a functional stack, a polymer insert and a second rigid substrate and wherein said second type are layers of the polyethylene terephthalate (PET) type.

33. The electrochromic window according to claim 32, wherein said first and second rigid substrate comprises one of glass and polycarbonate and wherein said polymer insert is one of polyurethane, polyvinyl butyral and ethylene vinyl acetate, with preferably the following, in order, composition of glass, a functional stack, ethylene vinyl acetate or polyurethane and a second glass.

* * * * *